(12) United States Patent
Ge et al.

(10) Patent No.: US 10,481,094 B2
(45) Date of Patent: Nov. 19, 2019

(54) TOTAL INTERNAL REFLECTION FLUORESCENCE IMAGING SYSTEM AND SEQUENCING DEVICE

(71) Applicant: GeneMind Biosciences Company Limited, Shenzhen, Guangdong (CN)

(72) Inventors: Liangjin Ge, Shenzhen (CN); Luyang Zhao, Shenzhen (CN); Ping Wu, Shenzhen (CN); Qin Yan, Shenzhen (CN)

(73) Assignee: GeneMind Biosciences Company Limited, Shenzhen (CN)

( * ) Notice: Subject to any disclaimer, the term of this patent is extended or adjusted under 35 U.S.C. 154(b) by 0 days.

(21) Appl. No.: 15/752,417

(22) PCT Filed: Sep. 6, 2016

(86) PCT No.: PCT/CN2016/098241
§ 371 (c)(1),
(2) Date: Feb. 13, 2018

(87) PCT Pub. No.: WO2017/041703
PCT Pub. Date: Mar. 16, 2017

(65) Prior Publication Data
US 2019/0011365 A1 Jan. 10, 2019

(30) Foreign Application Priority Data

Sep. 7, 2015 (CN) .......................... 2015 1 0562591

(51) Int. Cl.
*G01N 21/64* (2006.01)
*G02B 21/06* (2006.01)
(Continued)

(52) U.S. Cl.
CPC ....... *G01N 21/6452* (2013.01); *G01N 21/648* (2013.01); *G01N 21/6458* (2013.01);
(Continued)

(58) Field of Classification Search
CPC .......................... G01N 21/6457; G01N 21/64
(Continued)

(56) References Cited

U.S. PATENT DOCUMENTS

| 5,136,149 A | 8/1992 | Fujiwara et al. |
| 6,136,149 A | 10/2000 | Vallius |

(Continued)

FOREIGN PATENT DOCUMENTS

| CN | 102405431 A | 4/2012 |
| CN | 202975465 U | 6/2013 |

(Continued)

*Primary Examiner* — David P Porta
*Assistant Examiner* — Meenakshi S Sahu
(74) *Attorney, Agent, or Firm* — Seed Intellectual Property Law Group LLP

(57) ABSTRACT

The present disclosure discloses a total internal reflection fluorescence imaging system and a sequencing device. The total internal reflection fluorescence imaging system includes a first imaging system and a second imaging system. The first imaging system includes N separate laser light paths. The second imaging system determines the changes of the height of the sample by means of the differences of the positions at which the second receiving device acquires the second images, and performs automatic compensation according to the changes of the height of the sample, so as to ensure that the sample is always at a focused position. The embodiment can perform light path adjustment of the N separate laser light paths respectively by means of the second imaging system, so as to realize that the N separate laser light paths have the same penetration depth. Therefore no further light path adjustment is required when switching between different light sources, thus saving the time consuming for light path adjustment.

12 Claims, 3 Drawing Sheets

(51) Int. Cl.
  *G02B 21/16* (2006.01)
  *G02B 21/18* (2006.01)
  *G02B 21/00* (2006.01)
  *G02B 21/24* (2006.01)
  *G02B 27/14* (2006.01)

(52) U.S. Cl.
  CPC ......... *G02B 21/0076* (2013.01); *G02B 21/06* (2013.01); *G02B 21/16* (2013.01); *G02B 21/18* (2013.01); *G02B 21/245* (2013.01); *G02B 27/141* (2013.01); *G01N 2021/6419* (2013.01)

(58) Field of Classification Search
  USPC ...................................................... 250/458.1
  See application file for complete search history.

(56) References Cited

U.S. PATENT DOCUMENTS

| | | |
|---|---|---|
| 9,310,598 B2 | 4/2016 | Hing et al. |
| 9,606,342 B2 | 3/2017 | Cooper |
| 2002/0036824 A1 | 3/2002 | Sasaki |
| 2003/0044967 A1 | 3/2003 | Heffelfinger et al. |
| 2006/0026408 A1 | 2/2006 | Morris et al. |
| 2008/0087826 A1 | 4/2008 | Harris et al. |
| 2009/0213376 A1 | 8/2009 | Takatsuka |
| 2010/0193704 A1* | 8/2010 | Pratt ..................... G01J 3/4406 250/459.1 |
| 2011/0294116 A1 | 12/2011 | Huang |

FOREIGN PATENT DOCUMENTS

| | | |
|---|---|---|
| CN | 103384845 A | 11/2013 |
| CN | 104293648 A | 1/2015 |
| CN | 104316506 A | 1/2015 |
| CN | 104568877 A | 4/2015 |
| CN | 105241853 A | 1/2016 |
| JP | 2005-352030 A | 12/2005 |
| JP | 2010-113305 A | 5/2010 |
| JP | 2012-3198 A | 1/2012 |

* cited by examiner

TOTAL INTERNAL REFLECTION FLUORESCENCE IMAGING SYSTEM AND SEQUENCING DEVICE

CROSS REFERENCE TO RELATED APPLICATION

This application claims priority to Chinese Patent Application No. 201510562591.6, filed on Sep. 7, 2015, the entire content of which is incorporated herein in its entirety.

FIELD

The present disclosure relates to the field of optical technology, and more particularly relates to a total internal reflection fluorescence imaging system and a sequencing device.

BACKGROUND

With the development of single molecule imaging technology, researchers can observe the extension of a single base in the DNA/RNA chain, which greatly facilitates the development of the third generation gene sequencing technology-single molecule sequencing technology. By adding one base at each time to a complementary sequence of the object to be tested, the complementary strand is continuously extended, and finally we will obtain the entire gene sequence of the strand to be tested. Compared with the current popular second generation gene sequencing technologies, single molecule sequencing technology does not require polymerase chain reaction (PCR) amplification, therefore reducing the sequencing error rate.

In order to achieve single-molecule sequencing, many methods have been tried, such as column separation, radio-isotope labeling, and the like. However, these methods do not have the resolution required for single molecule sequencing. Fluorescence microscopy has become the primary method of single molecule sequencing due to its higher resolution, lower cost and simplicity of operation. There are three common methods of fluorescence microscopy: epi-fluorescence microscopy, confocal fluorescence microscopy and total internal reflection fluorescence (TIRF) microscopy. Resolution of the confocal and TIRF imaging is higher than that of epi-fluoresence imaging, while confocal imaging requires a long time to scan for forming an image, such that it is relatively not suitable for single molecule sequencing. The light path and light path adjustment of the current total internal reflection fluorescence microscopes need improvement.

SUMMARY

In view of the defects of the prior art, the embodiment of the present disclosure provides a total internal reflection fluorescence imaging system and a sequencing device which is convenient to operate.

An embodiment of the present disclosure provides a multi-path total internal reflection fluorescence imaging system, which includes: a first imaging system and a second imaging system; the first imaging system includes N separate laser light paths, an objective lens, and a first receiving device, where N is an integer greater than one, each of the laser light path is configured to generate light to enter the objective lens, the light passing through the objective lens illuminates a sample to excite the sample to emit fluorescence, the fluorescence passes through the objective lens and enters the first receiving device to form a first image; the second imaging system includes a light emitting source, the objective lens, and a second receiving device. The light emitting source is configured to emit light to enter the objective lens, the light passing through the objective lens illuminates the sample and is reflected, the reflected light passes through the objective lens and enters the second receiving device to form a second image.

In one embodiment of the present disclosure, the first imaging system further includes N first light sources, a reflecting mirror, and N first dichroic mirrors, each of the N first light sources is corresponding to one of the N first dichroic mirrors, the N separate laser light paths are composed by the N first light sources, the reflecting mirrors, and the N first dichroic mirrors, light generated by each of the laser light path is emitted from the first light source, the light emitted from the first light source is reflected by the reflecting mirror to enter the first dichroic mirror, the first dichroic mirror reflects the light into the objective lens; the second imaging system further includes a compensation lens and a second dichroic mirror, the light emitting source is a second light source, light emitted from the second light source enters the second dichroic mirror through the compensation lens, the second dichroic mirror reflects the light into the objective lens; wherein the objective lens, the first dichroic mirror, the second dichroic mirror and the first receiving device are configured along a single linear optical axis.

In one embodiment of the present disclosure, the first light source includes a laser, a diverging lens, a collimating lens, a first bandpass filter, a field stop, and a third dichroic mirror; wherein all of optical members constituting the first light source are configured along a single linear optical axis.

In one embodiment of the present disclosure, the lasers included in the N first light source are lasers of different operating wavelengths.

In one embodiment of the present disclosure, optical members included in the N first light source is corresponding to lasers of different operating wavelengths included in the N first light sources.

In one embodiment of the present disclosure, the first receiving device includes a tube lens, a second bandpass filter, and an electron multiplying camera; wherein optical members constituting the first receiving device are configured along a single linear optical axis.

In one embodiment of the present disclosure, the first dichroic mirror and the third dichroic mirror form an angle of 45 degree to the horizontal direction.

In one embodiment of the present disclosure, the second dichroic mirror forms an angle of 135 degree to the horizontal direction.

In one embodiment of the present disclosure, the objective lens is a total internal reflection objective.

In one embodiment of the present disclosure, the light emitting source is an LED light source.

The total internal reflection fluorescence imaging system provided by the embodiment of the present disclosure includes a first imaging system and a second imaging system. The first imaging system includes N separate laser light paths. The second imaging system determines the change of the height of the sample by means of the differences of the positions at which the second receiving device acquires the second images, and performs automatic compensation according to the changes of the height of the sample, so as to ensure that the sample is always at a focused position. The embodiment can perform light path adjustment of the N separate laser light paths respectively by means of the second imaging system, so as to realize that the N separate laser light paths have the same penetration depth. Compared to the prior art, the embodiment does not need to adjust the light path when switching between different light sources, thus saving the time required for light path adjustment.

An embodiment of the present disclosure provides a sequencing device, which includes the imaging system as described in any one of the preceding embodiments.

In the sequencing device provided by the embodiment of the present disclosure, the total internal reflection fluorescence imaging system includes a first imaging system and a second imaging system. The first imaging system includes N separate laser light paths. The second imaging system determines the change of the height of the sample by means of the differences of the positions at which the second receiving device acquires the second images, and performs automatic compensation according to the changes of the height of the sample, so as to ensure that the sample is always at a focused position. The embodiment can perform light path adjustment of the N separate laser light paths respectively by means of the second imaging system, so as to realize that the N separate laser light paths have the same penetration depth. Compared to the prior art, the embodiment does not need to adjust the light path when switching between different light sources, thus saving the time required for light path adjustment.

BRIEF DESCRIPTION OF THE DRAWINGS

To illustrate the technical solutions according to the embodiments of the present disclosure or in the prior art more clearly, the accompanying drawings for describing the embodiments or the prior art are introduced briefly in the following. The accompanying drawings in the following description are only some embodiments of the present disclosure, and persons of ordinary skill in the art can derive other obvious variations from the accompanying drawings without creative efforts.

DETAILED DESCRIPTION OF THE EMBODIMENTS

In order to make the above objects, features and advantages of the present disclosure become more apparent, the specific embodiments will be described in detail in combination with the accompanying drawings. It should be noted that the specific embodiments described herein are merely illustrative and are not intended to limit the invention.

Figure 1:
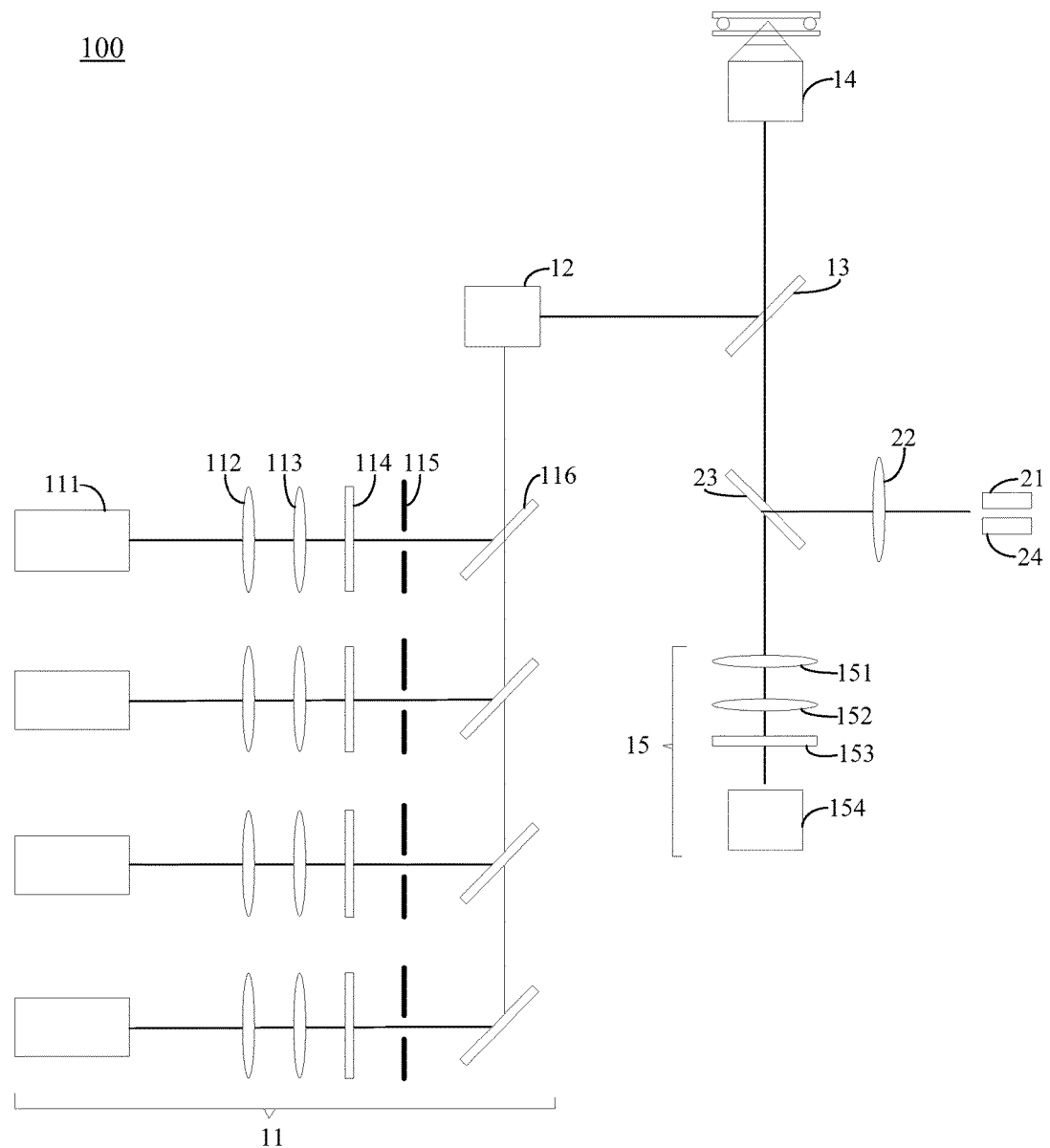
FIG. 1 is aschematic diagram of a total internal reflection fluorescence imaging system according to an embodiment of the present disclosure.
Figure 2:
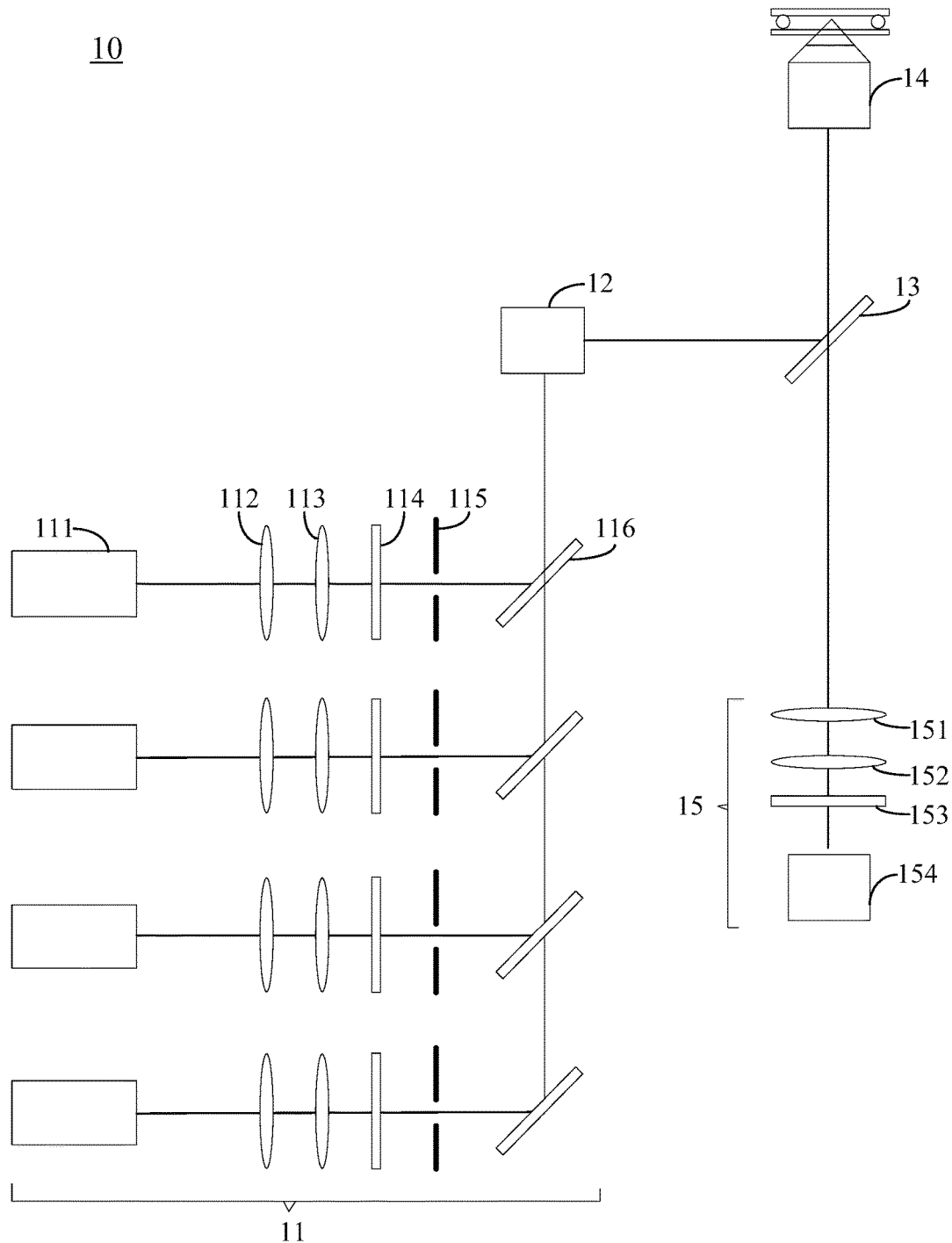
FIG. 2 is aschematic diagram of a first imaging system of a total internal reflection fluorescence imaging system according to an embodiment of the present disclosure.
Figure 3:
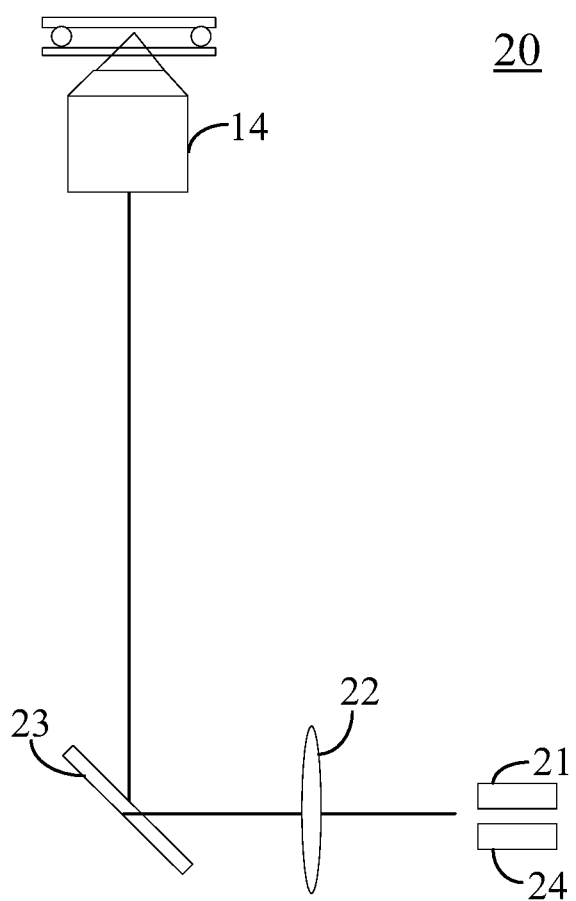
FIG. 3 is aschematic diagram of a second imaging system of a total internal reflection fluorescence imaging system according to an embodiment of the present disclosure.

FIG. 1 is a schematic diagram of a total internal reflection fluorescence imaging system 100 according to an embodiment of the present disclosure. As shown in FIG. 1, the total internal reflection fluorescence imaging system 100 includes a first imaging system 10 (as shown in FIG. 2) and a second imaging system 20 (as shown in FIG. 3).

The first imaging system 10 includes N separate laser light paths, an objective lens 14, and a first receiving device 15, where N is an integer greater than one. Each of the laser light path is configured to generate light to enter the objective lens 14. The light passing through the objective lens 14 illuminates on a sample to excite the sample to emit fluorescence. The fluorescence passes through the objective lens 14 and enters the first receiving device 15 to form a first image. The second imaging system 20 includes a light emitting source 21, the objective lens 14, and a second receiving device 24. The light emitting source 21 is configured to emit light to enter the objective lens 14. The light passing through the objective lens 14 illuminates the sample and is reflected. The reflected light passes through the objective lens 14 and enters the second receiving device 24 to form a second image.

Specifically, in the illustrated embodiment, the first imaging system 10 further includes N first light sources 11, a reflecting mirror 12, and N first dichroic mirrors 13. Each of the N first light sources 11 is corresponding to one of the N first dichroic mirrors 13. The N separate laser light paths are composed by the N first light sources 11, the reflecting mirrors 12, and the N first dichroic mirrors 13. The light generated by each of the laser light path is emitted from the first light source 11, and the light emitted from the first light source 11 is reflected by the reflecting mirror 12 to enter the first dichroic mirror 13. The first dichroic mirror 13 reflects the light into the objective lens 14. The light passing through the objective lens 14 illuminates the sample in the item placement area to excite the sample to emit fluorescence. The fluorescence passes through the objective lens 14 and the first dichroic mirror 13, and enters the first receiving device 15 to form a first image.

The second imaging system 20 further includes a compensation lens 22 and a second dichroic mirror 23. The light emitting source 21 is a second light source 21. The light emitted from the second light source 21 enters the second dichroic mirror 23 through the compensation lens 22. The second dichroic mirror 23 reflects the light into the objective lens 14. The light passing through the objective lens 14 illuminates the sample and is reflected. The reflected light passes through the objective lens 14 and the second dichroic mirror 23 and enters the second receiving device 24 to form a second image. The objective lens 14, the first dichroic mirror 13, the second dichroic mirror 23 and the first receiving device 15 are configured along a single linear optical axis. Such configuration makes the total internal reflection fluorescence imaging system more compact and facilitates the miniaturization of the total internal reflection fluorescence imaging system.

Dichroic mirror, also known as two-color mirror, is transmissive almost with respect to light of a certain wavelength, while it is reflective almost with respect to light of other wavelengths. Therefore, when the light is reflected into the first dichroic mirror 13 by the reflecting mirror 12, the light can be completely reflected into the objective lens 14. When fluorescence passes through the objective lens 14 and the first dichroic mirror 13, the light can be completely transmitted into the first receiving device 15.

The objective lens 14 is a total internal reflection objective, such that the sample in the item placement area is excited by the evanescent wave generated by the total internal reflection, thus fluorophores within a thin layer of hundreds of nanometer thickness of the surface of the sample are excited to emit fluorescence.

In one embodiment of the present disclosure, the first imaging system 10, referring to FIG. 2, a laser included in one first light sources 11 of the N first light sources 11 is turned on, light emitted from the first light source 11 passes through a series of optical members to the first dichroic mirror 13 (the first dichroic mirror 13 is the first dichroic mirror corresponding to the laser that is switched on). The laser is reflected by the first dichroic mirror 13 into the objective lens 14. The laser passes through the objective lens 14 and generates evanescent wave to excite the sample placed in the item placement area, such that fluorophores within the thin layer of hundreds of nanometer thickness of the surface of the sample are excited to emit fluorescence. The generated fluorescence passes through the objective lens 14 and enters the first dichroic mirror 13 to transmit, and then the generated fluorescence enters the first receiving device 15 to achieve single molecule detection.

The switching between different first dichroic mirrors 13 is performed by a mechanical wheel. The switching on of the laser and the switching of the first dichroic mirrors 13 are synchronous, and both of which can be performed automatically by running the software.

In one embodiment of the present disclosure, the second imaging system 20 is an automatic focusing system, referring to FIG. 3, the second light source 21 is an LED light source. The light emitted from the second light source 21 enters the second dichroic mirror 23 through the compensation lens 22 and is reflected by the second dichroic mirror 23 into the objective lens 14. The light passing through the objective lens 14 is focused on the sample and is reflected by the sample. The reflected light passes through the same path (i.e., passing through the objective lens 14, entering the second dichroic mirror 23 and reflected by the second dichroic mirror 23) and enters the second receiving device 24 to form a second image. The automatic focusing system determines the changes of the height of the sample by the differences of the positions of the second images formed at the second receiving device 24. The automatic focusing system performs automatic compensation according to the changes of the height of the sample to ensure that the sample is always at a focused position.

Furthermore, the first light source 11 includes a laser 111, a diverging lens 112, a collimating lens 113, a first bandpass filter 114, a field stop 115, and a third dichroic mirror 116, wherein all of optical members constituting the aforementioned first imaging system 11 are configured along a single linear optical axis.

The working principle of the first light source 11 is that: the laser 111 emits laser and passes through the diverging lens 112 such that the spot of the laser becomes larger. Then, the collimator lens 113 re-parallelizes the divergent laser. The parallel laser passes through the first bandpass filter 114 to filter out the light whose wavelength deviates from the laser center. Then the laser passes through the field stop 115 such that the spot size may be optimized. Finally, the laser is reflected into the reflecting mirror 12 by the third dichroic mirror 116.

Furthermore, the lasers included in the N first light sources are lasers of different operating wavelengths.

Furthermore, optical members included in the N first light source is corresponding to lasers of different operating wavelengths included in the N first light sources.

In the illustrated embodiment, since lasers included in the N first light sources 11 are lasers of different operating wavelengths, the first bandpass filter 114 is configured to filter out the light whose wavelength deviates from the laser center, and the third dichroic mirror 116 is configured to be transmissive almost with respect to light at a certain wavelength, the first bandpass filter 114 and the third dichroic mirror 116 required for lasers of different operating wavelengths are also different. For example, as for a 589 mm laser and a 1064 mm laser, the bandpass filter is transmissive with respect to a specific light and cut off the other light, the first bandpass filter 114 corresponding to the 589 mm laser is configured to filter out the light of a wavelength deviates from 589 mm, i.e., only the light of a wavelength range in 589±preset nanometer is allowed. The first bandpass filter 114 corresponding to the 1064 mm laser is configured to filter out the light of a wavelength deviates from 1046 mm, i.e., only the light of a wavelength range in 1046± preset nanometer is allowed. The preset nanometer may be 10 nm, 20 nm, 40 nm, 55 nm or other values. It can be seen that the first bandpass filter 114 corresponding to the 589 mm laser does not apply to the first bandpass filter 114 corresponding to the 1064 mm laser. Thus, the N first light sources 11 include different first bandpass filters 114. Of course, the first bandpass filters 114 included in the N first light sources 11 may be the same, such as lasers with very close center wavelengths. For example, as for a 589 mm laser and a 1064 mm laser, the third dichroic mirror 116 corresponding to the 589 mm laser is configured to be transmissive almost with respect to the light of a wavelength range in 589± preset nanometer, the third dichroic mirror 116 corresponding to the 1064 mm laser is configured to be transmissive almost with respect to the light of a wavelength range in 1064±preset nanometer. Thus, the N first light sources 11 include the third dichroic mirrors 116 are not identical. Of course, the third dichroic mirrors 116 included in the N first light sources 11 may be the same, such as lasers with very close center wavelengths.

The diverging lens 112 can enlarge the spot of the laser and the collimating lens 113 can re-parallelize the divergent laser. The operating wavelength of the diverging lens 112 and the collimating lens 113 is not limited, thus the diverging lens 112 and the collimating lens 113 in the laser of different operating wavelengths may be the same or different.

Furthermore, the first receiving device 15 includes a tube lens 151, a second bandpass filter 152, and an electron multiplying camera (Electron-multiplying CCD, EMCCD) 153, all of optical members constituting the aforementioned first receiving device 15 are configured along a single linear optical axis.

Furthermore, the first dichroic mirror 13 and the third dichroic mirror 116 form an angle of 45 degree to the horizontal direction.

Furthermore, the second dichroic mirror 23 forms an angle of 135 degree to the horizontal direction.

The total internal reflection fluorescence imaging system provided by the embodiment has the advantage of introducing N separate laser light paths. The N separate laser light paths can independently adjust the total internal reflection angle to achieve the same penetration depth, thereby omitting the time consuming light path adjustment steps. According to the experimental requirements, the N separate laser light paths can be alternately turned on, thus bringing great flexibility to the experimental design. In the illustrated embodiment, alternating illumination can be realized by switching the first dichroic mirrors 13 (For example, when a certain laser is turned on, the laser passes through a series of prisms and then reaches the first dichroic mirror 13. The first dichroic mirror 13 corresponding to the operating wavelength is selected according to the operating wavelength of the laser, thereby reflecting the laser into the objective lens 14. The switching between different first dichroic mirrors 13 is performed by the mechanical wheel. The switching on of the laser and the switching of the first dichroic mirrors 13 are synchronous, and both can be performed automatically by the software.). Therefore, only one EMCCD camera is required in the signal collection phase, which can both achieve the purpose of single molecule sequencing and save costs. In addition, the light path design is more concise, compact and convenient compared to the prior art, providing a great convenience for the operator.

According to the total internal reflection fluorescence imaging system provided by the embodiment, the N separate laser light paths can also be turned on simultaneously. Simultaneous illumination of N separate laser light paths requires N EMCCD cameras corresponding to the N separate laser light paths. For example, when the N lasers are turned on, the N lasers pass through a series of prisms and then reach the reflecting mirror 12 (polarization beamsplitter) to be divided into N lasers, which then reach the first dichroic mirrors 113 corresponding to the N lasers, respectively. Thus the N lasers are reflected into the objective lens 14 and then excited into N fluorescence by the objective lens 14. The N fluorescence enter the NEMCCD cameras respectively to realize imaging simultaneously.

A sequencing device is further provided by one embodiment, which includes the imaging system 100 as described in any one of the aforementioned embodiments.

In the sequencing device provided by the embodiment, the total internal reflection fluorescence imaging system 100 includes a first imaging system 10 and a second imaging system 20. The first imaging system 10 includes N separate laser light paths. The second imaging system 20 determines the change of the height of the sample by means of the differences of the positions at which the second receiving device acquires the second images, and performs automatic compensation according to the changes of the height of the sample, so as to ensure that the sample is always at a focused position. The embodiment can perform light path adjustment of the N separate laser light paths respectively by means of the second imaging system 20, so as to realize that the N separate laser light paths have the same penetration depth. Compared to the prior art, the embodiment does not need to adjust the light path when switching between different light sources, thus saving the time consuming light path adjustment.

Specifically, the sequencing device is a device for determining nucleic acid/protein sequences using optical imaging. The device for determining nucleic acid/protein sequences include, but are not limited to, the first, second and third generation sequencing platforms, such as single molecule sequencing platforms.

The foregoing descriptions are merely specific embodiments of the present disclosure, but are not intended to limit the protection scope of the present disclosure. It will be appreciated by those skilled in the art that the multi-path total internal reflection fluorescence imaging system of the present disclosure is applicable not only to single molecule sequencing but also to other molecular sequencing. Any replacement, variation and modification readily figured out by a person skilled in the art within the technical scope disclosed in the present disclosure shall all fall within the protection scope of the present disclosure.

What is claimed is:

1. A total internal reflection fluorescence imaging system, comprising:
a first imaging system, wherein the first imaging system comprises N separate laser light paths, an objective lens, a first receiving device, N first light sources, a reflecting mirror, and N first dichroic mirrors, N is an integer greater than one, each laser light path of the N separate laser light paths is configured to generate light to enter the objective lens, the light passing through the objective lens illuminates a sample to excite the sample to emit fluorescence, the fluorescence passes through the objective lens and enters the first receiving device to form a first image,
wherein each of the N first light sources corresponds to one of the N first dichroic mirrors,
wherein the N separate laser light paths are composed by the N first light sources, the reflecting mirror, and the N first dichroic mirrors, and
wherein light generated in each of the laser light paths is emitted from the first light source, the light emitted from the first light source is reflected by the reflecting mirror to enter the first dichroic mirror, the first dichroic mirror reflects the light into the objective lens; and
a second imaging system, wherein the second imaging system comprises a light emitting source, the objective lens, and a second receiving device, the light emitting source is configured to emit light to enter the objective lens, the light passing through the objective lens illuminates the sample and is reflected, the reflected light passes through the objective lens and enters the second receiving device to form a second image.

2. An imaging system according to claim 1,
wherein the second imaging system further comprises a compensation lens and a second dichroic mirror, the light emitting source is a second light source, light emitted from the second light source enters the second dichroic mirror through the compensation lens, the second dichroic mirror reflects the light into the objective lens;
wherein the objective lens, the first dichroic mirror, the second dichroic mirror and the first receiving device are configured along a single linear optical axis.

3. An imaging system according to claim 2, wherein the first light source comprises a laser, a diverging lens, a collimating lens, a first bandpass filter, a field stop, and a third dichroic mirror, wherein all of optical members constituting the first light source are configured along a single linear optical axis.

4. An imaging system according to claim 3, wherein the lasers comprised in the N first light sources are lasers of different operating wavelengths.

5. An imaging system according to claim 4, wherein optical members comprised in the N first light sources are corresponding to lasers of different operating wavelengths comprised in the N first light sources.

6. An imaging system according to claim 1, wherein the first receiving device comprises a tube lens, a second bandpass filter, and an electron multiplying camera, wherein all of optical members constituting the first receiving device are configured along a single linear optical axis.

7. An imaging system according to claim 6, wherein the first light source comprises a third dichroic mirror and wherein the first dichroic mirror and the third dichroic mirror form an angle of 45 degree to the horizontal direction.

8. An imaging system according to claim 2, wherein the second dichroic mirror forms an angle of 135 degree to the horizontal direction.

9. An imaging system according to claim 1, wherein the objective lens is a total internal reflection objective.

10. An imaging system according to claim 1, wherein the light emitting source is an LED light source.

11. A sequencing device, comprising an imaging system according to claim 1.

12. A sequencing device, comprising an imaging system according to claim 2.

* * * * *